US008444582B2

(12) United States Patent
Gobet

(10) Patent No.: US 8,444,582 B2
(45) Date of Patent: May 21, 2013

(54) DEVICE FOR ASSISTING IN THE SELECTION OF A COMPRESSIVE ORTHOSIS BY SIMULATING ITS EFFECTS UPON THE HEMODYNAMICS OF THE VENOUS RETURN

(75) Inventor: Arnaud Gobet, Paris (FR)

(73) Assignee: Laboratoires Innothera, Arceuil (FR)

( * ) Notice: Subject to any disclaimer, the term of this patent is extended or adjusted under 35 U.S.C. 154(b) by 1398 days.

(21) Appl. No.: 11/884,475

(22) PCT Filed: Feb. 3, 2006

(86) PCT No.: PCT/FR2006/000244
§ 371 (c)(1),
(2), (4) Date: May 23, 2008

(87) PCT Pub. No.: WO2006/087442
PCT Pub. Date: Aug. 24, 2006

(65) Prior Publication Data
US 2009/0055148 A1    Feb. 26, 2009

(30) Foreign Application Priority Data
Feb. 16, 2005    (FR) .................................... 05 01569

(51) Int. Cl.
*A61F 5/00* (2006.01)
*A61F 13/00* (2006.01)
*G06F 17/00* (2006.01)

(52) U.S. Cl.
USPC .................................... 602/2; 602/60; 701/11

(58) Field of Classification Search ......... 703/11; 705/2, 705/3
See application file for complete search history.

(56) References Cited

U.S. PATENT DOCUMENTS
7,966,197 B2 * 6/2011 Bassez et al. ..................... 705/3

FOREIGN PATENT DOCUMENTS
FR    2 852 421 A    9/2004

OTHER PUBLICATIONS
"Programme Final Cahier Des Resumes" Societe Francaise de Medecine Vascularie, Congres Annuel De Vasculis 2004, Sep. 9-11, 2004, Lyon, France 'Online! (URL:http://www.angioweb.fr/SFMW.pdf).
Chu, T-M et al., "Three-dimensional finite element stress analysis of the polypropylene, ankle-foot orthosis: static analysis," Medical Engineering & Physics, Butterworth-Heinemann, GB, vol. 17, No. 5 Jul. 1995 pp. 372-379.
Syngellakis S., et al., "Assessment of the Non-Linear Behaviour of Plastic Ankle Foot Orthoses by the Finite Element Method," Proceedings of the Institution of Mechanical Engineers. Journal of Engineering in Medicine. Part H, Mechanical Engineering Publications Ltd, London GB, vol. 214, No. 5, Part H, 2000, pp. 527-539.
Cros F., et al., "A digital model for the venous junctions," Computer Methods in Biomechanics and Biomedical Engineering, Dec. 2002, pp. 421-429.

* cited by examiner

*Primary Examiner* — Kim M Lewis
(74) *Attorney, Agent, or Firm* — Jacobson Holman PLLC

(57) ABSTRACT

A device determines and displays compression values to be exerted by an orthosis upon the surface of a member and produces digital simulation (10) for simulating the action of the compression on the hemodynamics of venous return furnishing values of blood flow and/or of intravenous pressure at a number of points of a digital model representing the venous network of the leg of the member, which display is a value oriented graph containing a number of interconnected arcs, with each arc assigned a corresponding value of blood flow and/or intravenous pressure, and which compression values are furnished by simulation software based on morphological characteristics of the member and on dimensional and rheological characteristics of the orthosis.

6 Claims, 2 Drawing Sheets

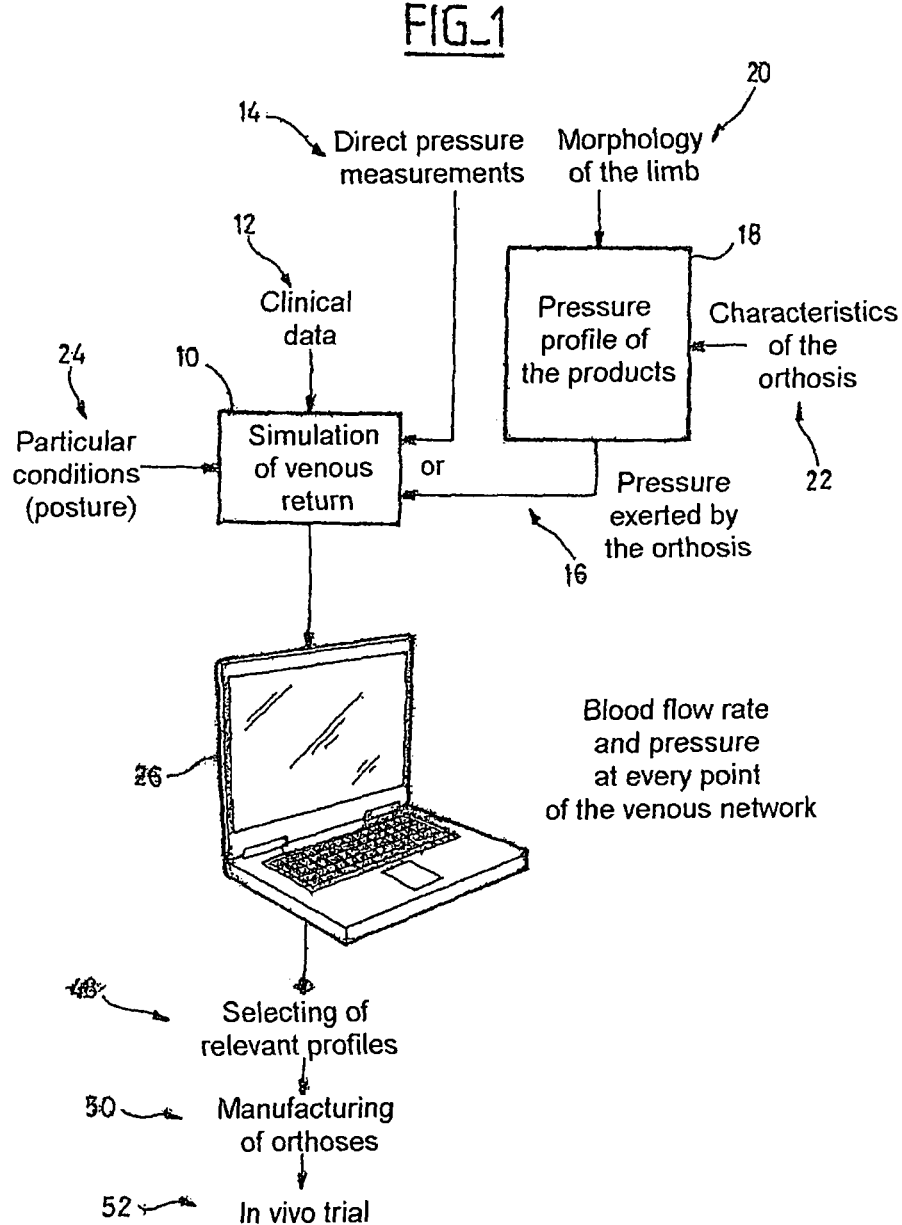

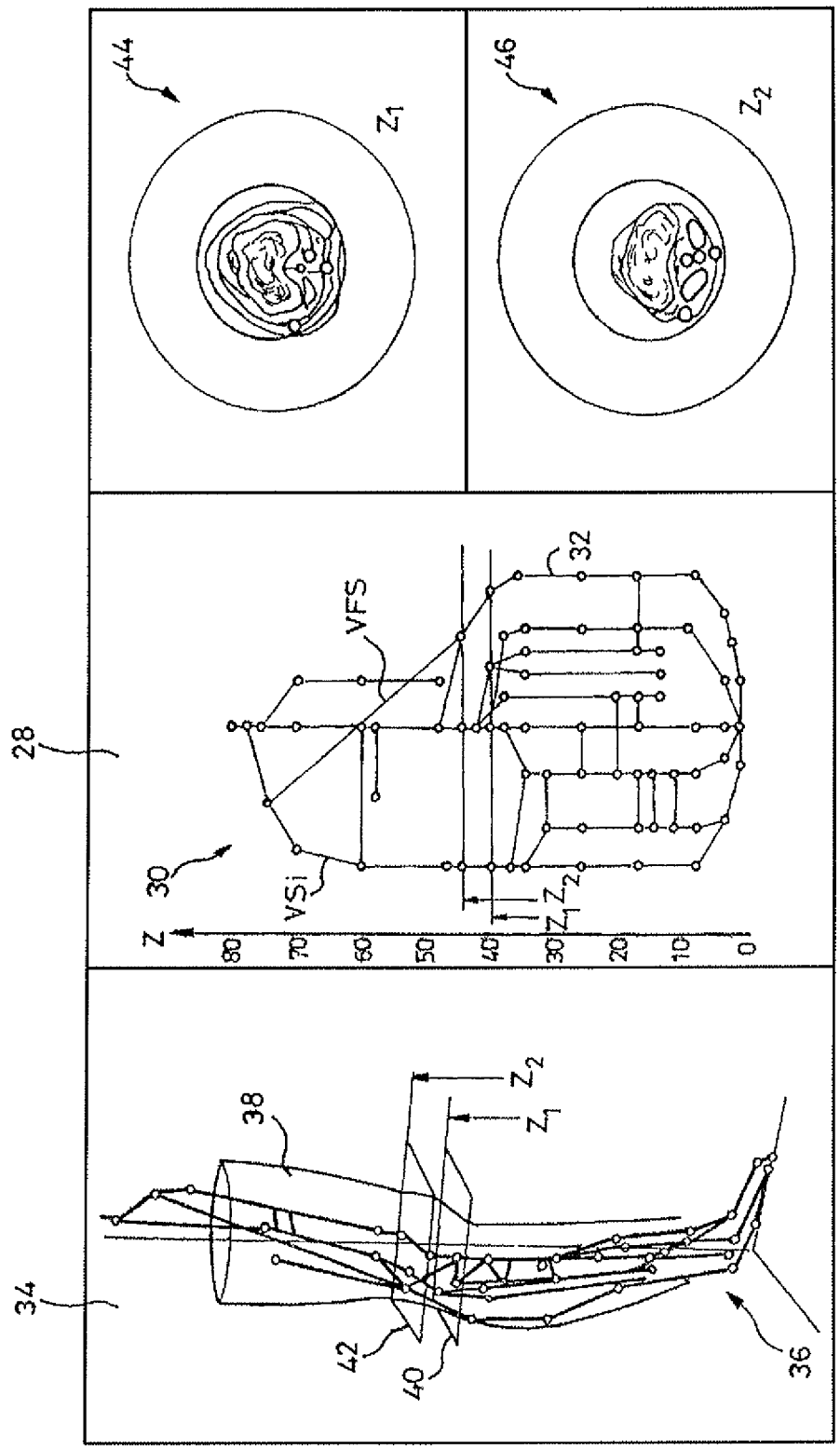
FIG_2

# DEVICE FOR ASSISTING IN THE SELECTION OF A COMPRESSIVE ORTHOSIS BY SIMULATING ITS EFFECTS UPON THE HEMODYNAMICS OF THE VENOUS RETURN

This is a 371 of PCT/FR2006/000244 filed 3 Feb. 2006.

The invention relates to a device for aiding the selection of a restraint orthosis and its adaptation to the morphology of a limb for which this orthosis is intended.

It relates more precisely to compressive orthoses, such as stockings, tights or socks, intended for the lower limbs.

The sought-after effect is a restraint/compression starting from the ankle to a therapeutic degree, with or without degression.

Fullana J M et al., *The Venous Return Simulator: An Effective Tool for Investigating the Effects of External Compression on the Venous Hemodynamics—First Results after Thigh Compression*, VASA 2005 34 describe a mathematical tool for simulating the venous return, which models the venous network of the lower part of the leg, decomposed into a plurality of segments each representative of a vessel portion.

This mathematical model is based on physiological and anatomical data describing the venous network of the lower limb. Once the topography of the network has been defined on the basis of these data, the model evaluates for each segment the flow rate and the pressure of the blood which circulates therein, taking account of the interaction between the various vessels on account of their diameter, their elasticity and the manner in which they are interconnected. The distribution of the flow rates and pressures in the network is calculated with boundary conditions comprising: the blood flow rate at input, starting from the region of the foot and various sources of microcirculatory origin; pressure conditions at the output point consisting of the common femoral vein; as well as a parameter relating to external compression possibly exerted on the limb.

The aforesaid article contains a comparison of the results provided by the mathematical model with measurements additionally performed on a population of patients within the framework of clinical trials, for variable restraint pressures applied by means of a pneumatic sleeve placed in the middle of the thigh. The comparison shows excellent agreement of the results over a wide range of pressure values applied by the sleeve.

This mathematical model does not however endeavor to evaluate the therapeutic . . . efficacy that could be expected in real situations with orthoses, such as stockings or tights commonly prescribed to patients suffering in particular from chronic venous insufficiency.

With these articles, the sought-after restraint/compression is obtained by the elastic material of the orthosis, typically a knitted mesh of very tight texture affording the sought-after therapeutic effect.

Accordingly, the mesh and the threads of the orthosis, as well as the dimensioning of the various mesh rows, are defined so as to apply various predetermined pressures at various altitudes of the leg, for example at the height of the ankle, at the start of the calf, at the level of the calf, at the popliteal space, etc. up to the top of the thigh in the case of a thigh stocking or a pair of tights. For a given altitude, the structure of the mesh row and the weft thread exert elastic restoring forces along the contour of the limb, which locally produce the desired restraint pressure at the surface of the limb.

The pressure is an essential factor for affording a satisfactory therapeutic effect. Thus, an inappropriate pressure profile can give rise locally to certain areas of excessive or, conversely, insufficient restraint of the limb (the "pressure profile" is the characteristic describing the average pressure exerted by the orthosis at a given height of the limb).

The pressure profiles are currently evaluated on the basis of models of wooden legs, for example legs termed "Hohenstein models", which do not correspond to morphological reality, in particular because these wooden leg models exhibit a circular contour in cross-section which leads to the application, for a given height, of a uniform pressure over the whole of this contour (according to Laplace's law, the pressure exerted locally at a point of the contour is inversely proportional to the radius of curvature of the contour at this point so that, for a constant curvature, the pressure is the same at all points of the contour). On the other hand, on a limb of a patient, having regard to the noncircular contours, the pressure is no longer exerted in as uniform a manner, so that the models currently used give only a relatively remote idea of the compression actually exerted at any point of the limb—and therefore, even more so, of the real therapeutic effect on the venous return that could be hoped for on the basis of such compression.

Hitherto, it has only been possible to evaluate the real efficacy of orthoses within the framework of clinical trials, involving an examination of the patient by a practitioner equipped with appropriate instrumentation: plethysmograph, echographic hardware, etc.

One of the aims of the invention is to propose a device making it possible to evaluate the efficacy of a given restraint on the venous return, so as to define optimized pressure profiles. This invention thus makes it possible to better target clinical investigations and to reduce their number.

On the basis of the optimal profiles thus found, a particular orthosis may be either chosen from a pre-existing range, or made to measure according to the morphological characteristics of the patient.

The invention is also aimed at proposing such a device that can be used as a tool for developing new ranges of orthoses, by simulating the action of a given restraint on the venous return of a typical population of patients.

The designer of orthoses will then be able, on the basis of the results of this simulation, to search for the profiles affording the best therapeutic effect, with pressure profiles that differ from and are possibly more complex than the profiles of the ranges available today.

To solve these problems and alleviate the limitations of the current techniques, the invention essentially proposes the use of a mathematical model such as that described in the aforesaid article by Fullana et al. no longer for theoretical purposes, but for the definition of pressure profiles allowing in particular: the selection of an appropriate orthosis from a pre-existing range; the definition of the manufacturing parameters of an orthosis made to measure for a given patient; or else the design of new types of orthoses exhibiting pressure profiles that differ from those of the products currently available on the market.

The device of the invention is a device comprising means such as those disclosed in the aforesaid article by Fullana et al., namely means for numerically simulating the action of the restraint on the hemodynamics of the venous return, able to deliver values of blood flow rate and/or intravenous pressure at a plurality of points of a numerical model representative of the sural venous network of a limb, and means for presenting said values of blood flow rate and/or intravenous pressure determined by these numerical simulation means.

In a manner characteristic of the invention, this device furthermore comprises means for: producing restraint pressure values capable of being exerted by the orthosis at the surface of the limb at a corresponding plurality of predetermined points, and applying the values thus produced as input to said numerical simulation means.

The means for producing the restraint pressure values can be measurement means, comprising a set of sensors for measuring the pressure exerted by the orthosis at the surface of the limb at the location of the sensor.

They can also be calculation means, comprising: means for establishing a first file of data representative of the morphological characteristics of the limb; means for establishing a second file of data representative of the dimensional and rheological characteristics of the orthosis; and restraint pressure mapping calculation means able to determine said restraint pressure values on the basis of the data of the first and second files.

Such means are for example disclosed, as such, by WO-A-2004/095342 (corresponding to FR-A-2 852 421), and also in a communication to the De Vasculis congress of the French Society of Vascular Medicine, 9-11 Sep. 2004, Lyons, France, pp. 10-11, but it had never been envisaged, until the priority date of the present application, to combine these means with a mathematical tool for simulating the venous return by applying, as proposed by the invention, the data produced by the calculation means as input parameter to the venous network model, so as to directly evaluate the therapeutic effect on the venous return that could be hoped for on the basis of a real orthosis.

In an advantageous embodiment, the numerical simulation means can receive as input a posture parameter and select or adapt the numerical model of the venous network as a function of this posture parameter.

Preferably, the means for presenting the values of blood flow rate and/or intravenous pressure comprise means for displaying a weighted directed graph comprising a plurality of interconnected arcs each representative of a vessel segment of the sural venous network, the display means associating with each arc of the graph a corresponding value of blood flow rate and/or intravenous pressure calculated by the numerical simulation means, for example with local application to each arc of the graph of a color coding representative of the corresponding value of blood flow rate and/or intravenous pressure. The display means can in particular produce a plane representation of the graph and/or, in overlay, a three-dimensional representation of the graph and of the surface of the limb.

An exemplary implementation of the device of the invention will now be described with reference to the appended drawings.

FIG. 1 illustrates, generally, the various means implemented by the device of the invention to allow the selection of a restraint orthosis and/or its adaptation to the morphology of the limb of a patient.

FIG. 2 shows the way in which it is possible to display in graphical form the results of the numerical simulation of the blood flow rate and pressure values.

In FIG. 1, the reference 10 designates a functional block implementing a piece of software for simulating the venous return, for example based on the mathematical model described in the article by Fullana et al. cited above.

This software is parametrized on the basis of clinical data 12 making it possible to define a topology of the venous network of the lower part of the leg, which corresponds to a typical model representative of a population of patients, possibly as a function of a clinical picture corresponding to a particular pathology with which one wishes more particularly to be concerned (for example dilated gemellus veins).

The software for simulating the venous return receives, as input, restraint pressure data (that is to say regarding the pressure exerted at the surface of the limb) at a plurality of points, in particular at several different altitudes so as to define a corresponding "pressure profile".

In a first implementation, these restraint pressures originate from direct measurements 14 obtained by means of devices which are in themselves known and which employ pressure sensors. The invention can in particular be used with the device described in WO-A-2004/000183 (Laboratoires Innothéra), which describes a tubular sleeve-shaped device making it possible to produce a predetermined restraint profile on a limb and simultaneously measuring the resulting pressure applied. Another usable device is that described in WO-A-1998/058605, which uses a template reproducing a reference leg and equipped with a network of sensors making it possible to measure the restraint pressures applied at a plurality of points of the template by an orthosis that is slipped over it.

In another implementation of the invention, the restraint pressure data applied as input to the simulation software 10 are data 16 arising from software for calculating a pressure profile 18, such as that described in the aforesaid WO-A-2004/095342 (Laboratoires Innothéra). This is a piece of software using, on the one hand, the morphological characteristics 20 of the limb to be studied and, on the other hand, the dimensional and rheological characteristics 22 of the orthosis, to calculate the restraint pressure values capable of being exerted by the orthosis on the limb at a plurality of points distributed according to a three-dimensional mesh representative of the surface of the limb.

The software for simulating the venous return 10, in addition to the restraint pressure values calculated 16, can also receive as input a parameter corresponding to a particular posture condition of the patient: orthostatic position, dorsal decubitus, walking, seated position, etc.

The simulation software 10, on the basis of these various input parameters, produces data representative of the intravenous pressure and/or blood flow rate at all points of the sural venous network, that is to say on each section of vessel of this network.

These data can be synthesized and displayed in graphical form on a screen 26.

FIG. 2 illustrates an exemplary display of the resulting data.

A first window 28 gives a plane representation of the graph modeling the venous network. This graph 30 is a directed and weighted graph formed of a plurality of interconnected arcs 32 each representative of a stretch of vessel. Each arc is parametrized as a function of the diameter and elasticity of the vessel. The model takes account of the blood flow at input from the region of the foot and various sources of microcirculatory origin, and of the pressure conditions at output in the internal saphenous vein ISV and the superficial femoral vein SFV.

According to the restraint applied at the surface of the limb, the practitioner will be able to evaluate visually and in an overall manner the depth-wise effect of this restraint, therefore the therapeutic effect as predicted by the model.

The flow rate and/or the pressure inside each vessel can be represented by a different color. If for example the lowest blood flow rates are displayed in blue, and the highest in red, by modifying the restraint pressure input data, the operator will immediately see the therapeutic effect of this restraint modification, not only in a global manner at the output of the sural network (as was the case hitherto), but also in a specific manner, and depth-wise, on such and such a section of vessel.

In another window 34 the simulation software displays a three-dimensional representation 36 of the plane graph 30 of the window 28. This three-dimensional perspective representation, with possibility of rotation under the user's control, is advantageously overlayed on a corresponding three-dimensional representation 38 of the surface of the limb, to facilitate reading. The operator can additionally designate horizontal sectional planes such as 40,42 at respective altitudes $Z_1$, $Z_2$ producing in respective windows 44, 46 a corresponding complete sectional representation of the limb with bones, vessels, ligaments, etc.

On the basis of these investigations and observations, the practitioner will then be able for example to define (step 48) which pressure profiles are the most relevant, that is to say those which afford the optimal therapeutic effect, and make orthoses exhibiting the corresponding dimensional and rheological characteristics (step 50) on the basis of these profiles.

This selection of profiles may be finally validated (step 52) by clinical trials performed in vivo on patients by means of appropriate kit.

The implementation of the invention affords numerous advantages with respect to the earlier procedure, in particular:
- possibility of studying the effect of a restraint on areas that are inaccessible to measurement, but which will be represented on the graph displayed by the simulation software;
- verification of the feasibility of clinical trial protocols;
- targeting of clinical trials that are actually to be carried out, with a considerable time saving insofar as selection of the relevant profiles is carried out a priori, and not a posteriori;
- considerable time saving for the development of new products better suited to their target, for example of products intended to treat specific pathologies of the sural venous network;
- possibility of searching for the best dose efficacy ratios (that is to say the depth-wise effect obtained as a function of the restraint applied at the surface), while avoiding in particular exerting, on certain areas, unnecessary restraints that are uncomfortable for the patient and perhaps even harmful, in order to concentrate the restraint on the regions where it, even moderate, affords a significant increase in the venous flow rate.

The invention claimed is:

1. A device for aiding the selection of a compressive restraint orthosis made of elastic or inelastic material and for evaluating a therapeutic effect upon venous return of the orthosis, and adaptation of the orthosis to morphological characteristic of a limb for which the orthosis is intended, the device comprising
    means for establishing a first file of data representative of the morphological characteristics of the limb,
    means for establishing a second file of data representative of the dimensional and rheological characteristics of the orthosis,
    restraint pressure mapping calculation means adapted to determine, on the basis of the data of the first and second files, restraint pressure values to be exerted by the orthosis at a surface of the limb at a corresponding plurality of predetermined points,
    means for numerically simulating action of the restraint on hemodynamics of the venous return, adapted to (i) receive as input restraint pressures computed by the mapping calculation means and (ii) deliver values of blood flow rate and/or intravenous pressure at a plurality of points of a numerical model representative of a sural venous network of a limb, and
    means for presenting the values of blood flow rate and/or intravenous pressure determined by the numerically simulating means,
whereby the device evaluates depth-wise therapeutic effect produced by the orthosis upon the venous return.

2. The device of claim 1, where the numerically simulating means are also able to receive as input a posture parameter and to select or adapt the numerical model of the sural venous network as a function of the posture parameter.

3. The device of claim 1, where the means for presenting the value of blood flow rate and/or intravenous pressure comprise means for displaying a weighted directed graph comprising a plurality of interconnected arcs each representative of a vessel segment of the sural venous network, the display means being able to associate with each arc of the graph a corresponding value of blood flow rate and/or intravenous pressure calculated by the numerically simulating means.

4. The device of claim 3, where the display means are able to apply locally to each arc of the graph a color coding representative of the corresponding value of blood flow rate and/or intravenous pressure.

5. The device of claim 3, where the display means comprise means able to produce a plane representation of the graph.

6. The device of claim 3, where the display means comprise means able to produce, in overlay, a three-dimensional representation of the graph and a three-dimensional representation of the surface of the limb.

* * * * *